United States Patent
Ajiki (10) Patent No.: US 9,241,685 B2
(45) Date of Patent: Jan. 26, 2016

(54) ULTRASONIC IMAGING APPARATUS AND THREE-DIMENSIONAL IMAGE DISPLAY METHOD USING ULTRASONIC IMAGE

(75) Inventor: Naoko Ajiki, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 439 days.

(21) Appl. No.: 13/814,371

(22) PCT Filed: Jul. 21, 2011

(86) PCT No.: PCT/JP2011/066516
§ 371 (c)(1),
(2), (4) Date: Feb. 5, 2013

(87) PCT Pub. No.: WO2012/017827
PCT Pub. Date: Feb. 9, 2012

(65) Prior Publication Data
US 2013/0142010 A1 Jun. 6, 2013

(30) Foreign Application Priority Data
Aug. 6, 2010 (JP) .................. 2010-177048

(51) Int. Cl.
*A61B 8/00* (2006.01)
*A61B 8/14* (2006.01)
(Continued)

(52) U.S. Cl.
CPC ... *A61B 8/14* (2013.01); *A61B 8/42* (2013.01); *A61B 8/4245* (2013.01); *A61B 8/4263* (2013.01); *A61B 8/463* (2013.01);
(Continued)

(58) Field of Classification Search
USPC .......................................................... 367/7
See application file for complete search history.

(56) References Cited

U.S. PATENT DOCUMENTS

| 7,375,455 B2 * | 5/2008 | Koizumi et al. ......... 310/316.02 |
| 8,094,894 B2 * | 1/2012 | Nagler et al. .............. 382/128 |

(Continued)

FOREIGN PATENT DOCUMENTS

| JP | 09-299364 | 11/1997 |
| JP | 11-113902 | 4/1999 |

(Continued)

OTHER PUBLICATIONS

International Search Report, International Application No. PCT/JP2011/066516, Filed Jul. 21, 2011, Mailed Aug. 30, 2011, ISA/Japanese Patent Office.

*Primary Examiner* — James Hulka
(74) *Attorney, Agent, or Firm* — Brundidge & Stanger, P.C.

(57) ABSTRACT

The ultrasonic imaging apparatus of the present invention is provided with a 3-dimensional image construction unit configured to construct a 3-dimensional image using plural ultrasonic tomographic images obtained when the ultrasonic probe is moved in a direction intersecting the direction of the ultrasonic tomographic images; and an ultrasonic probe moving direction setting unit configured to set the moving direction of the ultrasonic probe, using an ultrasonic tomographic image displayed on the screen of the display unit as a reference, in either a first direction which intersects with the direction of the tomographic image or a second direction of opposite orientation to the first direction; wherein the control unit controls the arrangement order of the plural ultrasonic tomographic images in the 3-dimensional image constructed in the 3-dimensional image construction unit according to the moving direction of the ultrasonic probe set by the moving direction setting unit of the ultrasonic probe.

17 Claims, 10 Drawing Sheets

(51) Int. Cl.
*G01S 15/89* (2006.01)
*G01S 7/52* (2006.01)
*A61B 8/08* (2006.01)

(52) U.S. Cl.
CPC .............. *A61B 8/466* (2013.01); *A61B 8/483* (2013.01); *G01S 7/52073* (2013.01); *G01S 7/52074* (2013.01); *G01S 15/8936* (2013.01); *G01S 15/8993* (2013.01); *A61B 8/467* (2013.01); *A61B 8/469* (2013.01)

(56) References Cited

U.S. PATENT DOCUMENTS

| | | | |
|---|---|---|---|
| 8,343,052 B2* | 1/2013 | Kawagishi et al. | 600/443 |
| 8,427,546 B2* | 4/2013 | Sato | 348/220.1 |
| 8,600,129 B2* | 12/2013 | Seko et al. | 382/128 |
| 2006/0250046 A1* | 11/2006 | Koizumi et al. | 310/317 |
| 2007/0156047 A1* | 7/2007 | Nagler et al. | 600/436 |
| 2009/0198133 A1* | 8/2009 | Kawagishi et al. | 600/443 |
| 2011/0091086 A1* | 4/2011 | Seko et al. | 382/131 |
| 2011/0273573 A1* | 11/2011 | Sato | 348/220.1 |

FOREIGN PATENT DOCUMENTS

| | | |
|---|---|---|
| JP | 11-253444 | 9/1999 |
| WO | 2006-059668 | 8/2006 |
| WO | 2012-017827 | 9/2012 |

* cited by examiner

ULTRASONIC IMAGING APPARATUS AND THREE-DIMENSIONAL IMAGE DISPLAY METHOD USING ULTRASONIC IMAGE

FIELD OF THE INVENTION

The present invention relates to an ultrasonic imaging apparatus for imaging an examination target using an ultrasonic probe, in particular to the ultrasonic imaging apparatus and the 3-dimensional image display method using an ultrasonic image which excels in operability and enables an operator to accurately display a desired image.

DESCRIPTION OF RELATED ART

An ultrasonic imaging apparatus is for imaging the inside of an object to be examined using an ultrasonic probe provided with transducers that transmits and receive ultrasonic waves, and is in heavy usage for making diagnosis as a non-invasive examination apparatus. An ultrasonic probe is generally provided with plural transducers arrayed therein in one direction, which are sequentially activated in the condition being applied to the surface of an examination object. The ultrasonic imaging apparatus, by sequentially activating plural ultrasonic transducers, transmits ultrasonic beams to the inside of the object, and measures the reflected echo signals from the inside of the object. The ultrasonic imaging apparatus obtains the information of the cross-sections (tomographic images) that includes element sequence and intersects orthogonally with the surface of the examination object by measuring the reflected echo signals from the inside of the object.

The information of the tomographic image obtained by the ultrasonic imaging apparatus is positionally comparative, since the information is acquired by an ultrasonic probe which is manually moved by an operator. Thus it is necessary to provide means to record the positional information of the ultrasonic probe and notify the operator of the recorded information.

In conventional ultrasonic imaging apparatuses, a direction marker such as a projection or a groove is provided on the ultrasonic probe, so that the operator can recognize whether the tomographic image displayed on a monitor is from the adverse side or the back side of the ultrasonic probe, or from which element sequence of the ultrasonic probe the tomographic image is obtained. Also, an orientation mark corresponding to the direction marker is overlapped and displayed on an image in a display screen.

In the case that the direction marker is provided on the adverse side of the ultrasonic probe, imaging is performed while the operator holds the ultrasonic probe so that the direction marker of the probe is positioned on the right side as viewed by the operator and the line of sight is set so that the tomographic image viewed from the operator's side is displayed, the orientation mark is displayed on the right side of the tomographic image (on the right side which is the same as the direction marker).

On the other hand, in the case that the surface of the ultrasonic probe where the direction marker is not provided is set as the back surface, imaging is performed while the operator holds the ultrasonic probe so that the direction marker of the probe is positioned on the right side as viewed by the operator and the line-of-sight direction is set so that the tomographic image viewed from the operator's side is displayed, the orientation mark is displayed on the left side of the tomographic image (on the left side being opposite from the direction marker).

In other words, switching from the adverse side to the back side or from the back side to the adverse side means that the line-of-sight direction is switched.

The operator can recognize the orientation of the line-of-sight direction, i.e. from which direction the tomographic image is viewed, by seeing whether or not the arrangement of the direction marker of the ultrasonic probe and the arrangement of the orientation mark on the screen are the same, and also can switch the line-of-sight direction.

Also, a body mark for showing the examination part or the posture of an object is generally displayed on the screen, and a probe mark showing the position and direction of the ultrasonic probe is displayed on the body mark.

Further, an ultrasonic imaging apparatus has been proposed which detects the position of the ultrasonic probe in a real space using a position sensor and automatically display the body mark in accordance with the posture of the object along with the position and direction of the probe mark (Patent Document 1).

In the mean time, an ultrasonic image apparatus provided with a function to obtain 3-dimensional images has been put to practical use (for example, Patent Document 2).

There are two major methods for obtaining 3-dimensional images such as the method disclosed in Patent Document 2. One method of obtaining 3-dimensional images is to oscillate transducers by setting the element sequence of the ultrasonic probe (transmitting source of ultrasonic waves) as the central axis. The other method for obtaining 3-dimensional images is to move the ultrasonic probe in parallel in the direction orthogonal to the element sequence using an actuator or manually.

In another method for obtaining 3-dimensional images, an operator collects image data by setting a region of interest on a 2-dimensional image (tomographic image), determining the size and direction of the tomographic plane (X-Y plane) and determining the size of Z-direction by setting the collecting distance, collecting time and collecting pitch, etc. of the Z-direction.

The Z-direction, i.e. the direction for moving a ultrasonic probe has two orientations of positive and negative (+Z direction and −Z direction) with respect to the X-Y plane in the scan plane of the ultrasonic probe. The orientation of the scan plane of the ultrasonic probe is either fixed in one direction or set to select one of two orientations that are determined based on the position of the direction marker in the ultrasonic probe.

For example, when the operator holds the ultrasonic probe such that the direction marker thereof is positioned on the right side, the direction for moving the probe from the front to the back is determined as +Z direction and the direction for moving the probe from the back to the front is determined as −Z direction. After such setting is performed, the operator executes imaging by moving the ultrasonic probe in the set direction.

Tomographic images are obtained in the respective positions in the moving direction of the ultrasonic probe. The ultrasonic imaging apparatus stores these tomographic images in a memory of 2-dimensional image frames in accordance with the moving direction, and constructs a 3-dimensional image (stereoscopic image). The constructed 3-dimensional image is displayed on a display screen along with the tomographic images.

PRIOR ART DOCUMENTS

Patent Documents

Patent Document 1: JP-A-2004-57379
Patent Document 2: JP-A-2000-333952

SUMMARY OF INVENTION

Technical Problem

In the case of obtaining data for 3-dimensional images by moving an ultrasonic probe as mentioned above, an operator needs to: (1) confirm the direction mark of the ultrasonic probe, i.e. set the line-of-sight direction, and (2) set (define) the moving direction.

However, during making diagnosis, there are cases that an operator changes the direction to apply a probe or the way to hold the probe in accordance with the change of the object's posture or movement of a region of interest, which could reverse the definition of the line-of-sight direction and the moving direction.

Also, when the operator performs the examination by inserting an ultrasonic probe into the body of an object, it is often difficult to set the line-of-sight direction. There is a possibility that the line-of-sight direction which is intended by the operator and the orientation in the display of the constructed 3-dimensional image are reversed.

Figure 10:
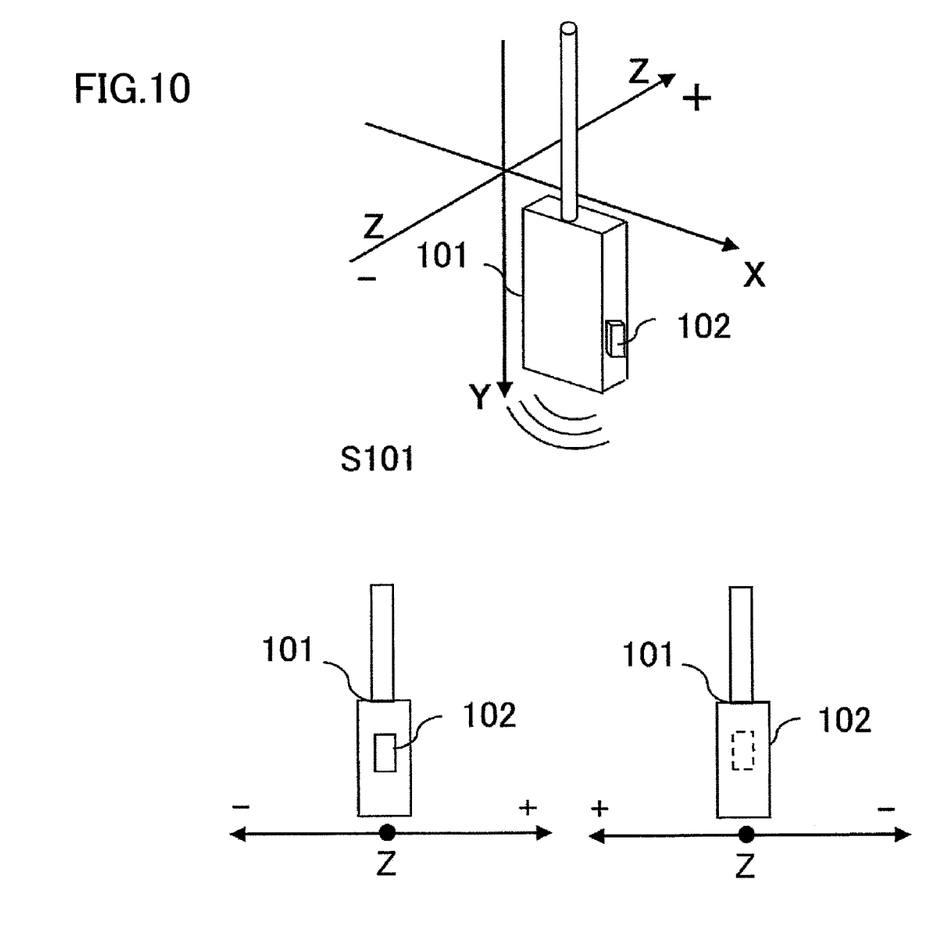
FIG. 10 is a view for explaining the method of defining the moving direction of an ultrasonic probe in an ultrasonic imaging apparatus.

For example, when the positional relationship is defined as shown in FIG. 10 and the moving direction of the ultrasonic probe is set in the condition that the operator holds the ultrasonic probe in the way that the direction marker is on the left side and the line-of-sight direction is opposite from the case of holding the probe on the right side (set in +Z direction or −Z direction), the ultrasonic imaging apparatus collects the tomographic images for a 3-dimensional image in accordance with the set moving direction, thus the constructed 3-dimensional image will be displayed as a mirrored image for the operator. If the operator misidentifies the displayed mirrored image as an actual image, it could lead to making wrong diagnosis.

The objective of the present invention is to provide the ultrasonic imaging apparatus capable of preventing operators from misidentifying directions in displayed images.

BRIEF SUMMARY OF THE INVENTION

In order to achieve the above-described objective, the ultrasonic imaging apparatus of the present invention is provided with a function to set the moving direction of an ultrasonic probe based on the image which is displayed on a screen and a function to construct and display a 3-dimensional image corresponding to the set direction.

More specifically, the ultrasonic imaging apparatus of the present invention comprises:
an ultrasonic probe;
a transmission/reception circuit configured to transmit and receive ultrasonic signals to/from an object to be examined via the ultrasonic probe;
an image construction unit configured to construct an ultrasonic tomographic image of an examination object using the received ultrasonic signals;
a display unit configured to display the ultrasonic image; and
a control unit configured to control the image construction unit and the display unit,
further comprising:
a 3-dimensional image construction unit configured to construct a 3-dimensional image using plural ultrasonic tomographic images that are obtained by moving the ultrasonic probe in the direction intersecting with the ultrasonic tomographic images: and
an ultrasonic probe moving direction setting unit configured to set a first direction, on the basis of the ultrasonic tomgoraphic image displayed on the screen of the display unit, which intersects with the displayed image and a second direction which is opposite to the first direction,
wherein the control unit controls the arrangement order of plural ultrasonic tomographic images in the 3-dimensional image which is constructed in the 3-dimensional construction unit in accordance with the moving direction of the ultrasonic probe set by the ultrasonic probe moving direction setting unit.

Also, the 3-dimensional image display method using the ultrasonic imaging apparatus of the present invention includes steps of:
transmitting/receiving ultrasonic signals to/from an object to be examined via an ultrasonic probe;
constructing an ultrasonic tomographic image of the object using the received ultrasonic signals; and
displaying the ultrasonic image,
further including steps of:
constructing a 3-dimensional image using plural ultrasonic tomographic images obtained when the ultrasonic probe is moved in the direction which intersects with the ultrasonic tomographic images;
setting a moving direction of the ultrasonic probe from among a first direction, on the basis of the ultrasonic tomographic image displayed on a screen, which intersects with the displayed tomographic image and a second direction which is opposite to the first direction; and
controlling the arrangement order of plural ultrasonic tomographic images in the constructed 3-dimensional image in accordance with the set ultrasonic probe moving direction.

Effect of the Invention

In accordance with the present invention, it is possible to provide the ultrasonic imaging apparatus capable of preventing an operator from misidentifying directions on display images.

DETAILED DESCRIPTION OF THE INVENTION

The embodiments of the ultrasonic imaging apparatus in the present invention will be described below referring to the diagrams.

Embodiment 1

Figure 1:
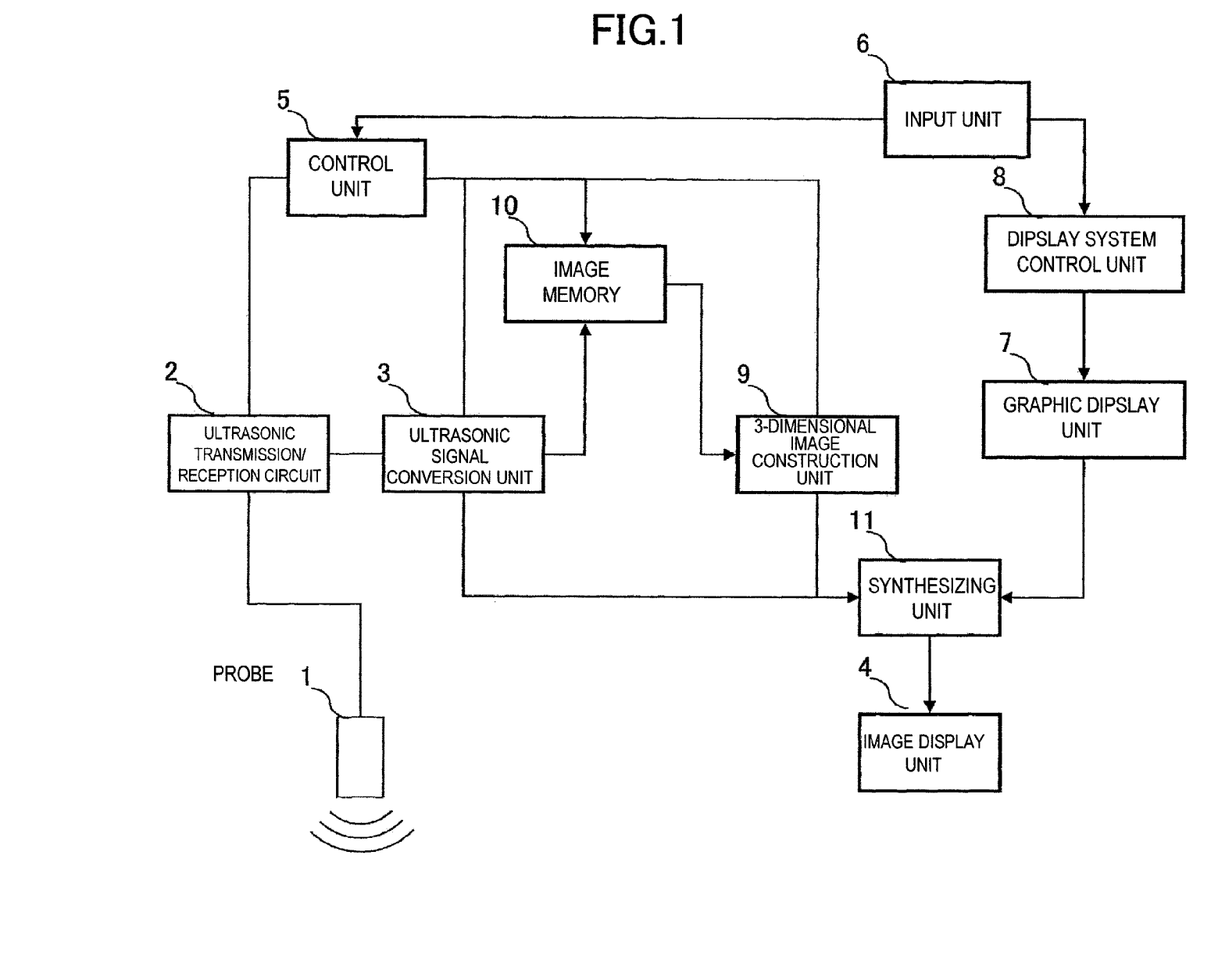
FIG. 1 is a block diagram showing the general outline of the ultrasonic imaging apparatus in a first embodiment.

FIG. 1 shows the general outline of the ultrasonic imaging apparatus in the present embodiment. The ultrasonic imaging apparatus comprises an ultrasonic probe 1 configured to transmit ultrasonic beams to an examination object (not shown in the diagram) and receive the reflected echo signals from the examination object, an ultrasonic transmission/reception circuit 2 configured to transmit ultrasonic signals to the ultrasonic probe 1 and receive the reflected echo signals from the ultrasonic probe 1, an ultrasonic signal conversion unit 3 configured to reconstruct the reflected echo signals into an ultrasonic image, an image display unit 4 configured to display the ultrasonic image which is reconstructed in the ultrasonic signal conversion unit 3, and a control unit configured to control the respective units including the ultrasonic transmission/reception circuit 2 and the ultrasonic signal conversion unit 3. The control unit 5 comprises an operation panel provided with a device such as a key or a trackball for receiving the input from an operator as an input unit 6 and a display unit for displaying GUI, etc. which are necessary for inputting information. The display unit of the input unit 6 can also function as an image display unit 4.

Further, the ultrasonic imaging apparatus of the present invention comprises a graphic display unit 7 (image storage unit) configured to store an orientation image to be displayed along with an ultrasonic image, a display system control unit configured to control, at the time of displaying the orientation images of the graphic display unit 7 on the image display unit 4, the position or orientation of the orientation image on a screen, a 3-dimensional image construction unit 9 configured to construct a 3-dimensional image using the ultrasonic image (tomographic image) which is created in the ultrasonic signal conversion unit 3 and an image memory 10 configured to accumulate tomographic images for constructing a 3-dimensional image. The tomographic images reconstructed in the ultrasonic signal conversion unit 3, a 3-dimensional image constructed in the 3-dimensional image construction unit 9 and orientation images of the graphic display unit 7 are synthesized by a synthesizing unit 11 and displayed on the image display unit 4. While the ultrasonic signal conversion unit 3 has the function of an image construction unit and the 3-dimensional image construction unit 9 is provided as a separate component in FIG. 1, the 3-dimensional image construction unit 9 can also be set as a function of an image construction unit.

Figure 2:
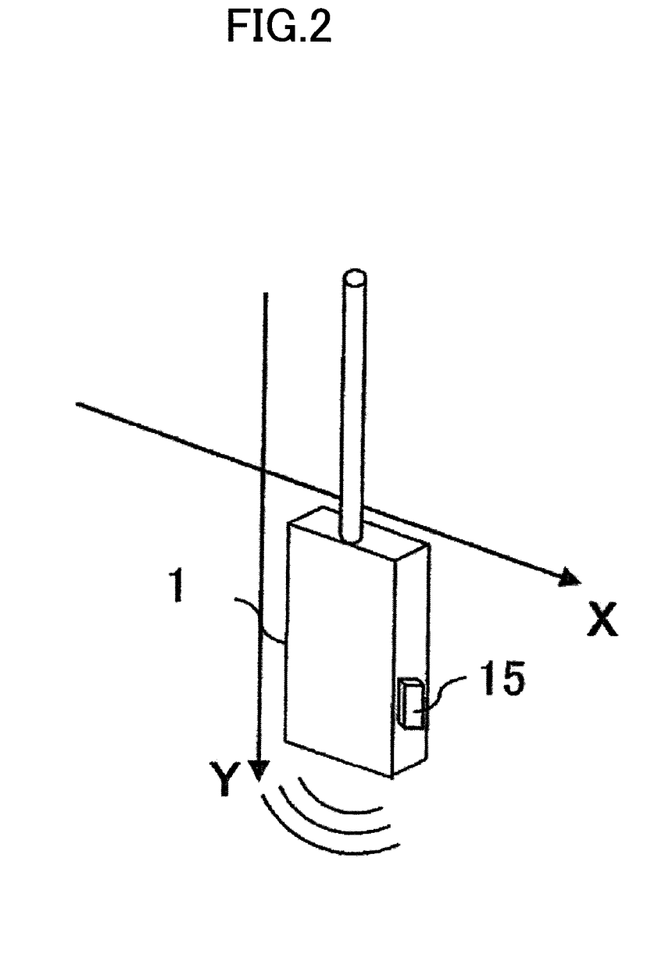
FIG. 2 is a perspective illustration showing the outer appearance of an ultrasonic probe.

There are various types of the ultrasonic probe 1 depending on areas or shapes of an examination target or the purpose of examinations. Though the kinds are not limited, the ultrasonic probe 1 is generally provided with plural transducers arrayed linearly or in arc-shape, and the transducers are set to be activated from one end to the other end at certain time intervals. As shown in FIG. 2, the ultrasonic probe 1 is provided with a projection or a groove as a marker 15 for identifying the adverse side and the back side of the surface (scan surface) which is determined by the scan direction (denoted by an arrow in the diagram) of an ultrasonic beam. A direction mark corresponding to the marker 15 is displayed on the tomographic image which is displayed on the image display unit 14, and the operator can identify, by this direction mark, from which side of the scan surface the displayed tomographic image is viewed. The direction for viewing the tomographic image is referred to as a line-of-sight direction.

There are types of the ultrasonic probe 1 that are provided with plural rows of element sequences, and the ultrasonic imaging apparatus of the present invention can adopt such type of an ultrasonic probe with plural sequences.

The configuration of the ultrasonic transmission/reception circuit 2 and the ultrasonic signal conversion unit 3 is the same as conventional ultrasonic imaging apparatuses, which comprises devices such as a pulse generation circuit configured to send out ultrasonic signals, a video amplifier configured to amplify the echo signals, and a DSC (Digital Scan Converter) configured to store A-mode signals as a digital amount and convert them into TV signals. Also, a device such as a Doppler circuit comprising a frequency analyzing unit may also be provided.

The control unit 5 controls the operation of the above-described ultrasonic transmission/reception circuit 2 and the ultrasonic signal conversion unit 3, and also controls the operation of the image memory 10 for storing tomographic images or the 3-dimensional image construction unit 9 in accordance with the condition at the time of 3-dimensional imaging which is input via the input unit 6, more specifically the setting of the moving direction of the ultrasonic probe 1. The input unit 6 has the function of the ultrasonic probe moving direction setting unit. The control operation by the control unit 5 will be described later in detail along with the operation of the ultrasonic imaging apparatus.

The input unit 6 can adopt various input devices such as a touch panel, a remote controller and a foot switch, besides a key or a trackball provided on the operation panel.

The graphic display unit 7 stores the orientation image to be an index for the operator along with a tomographic image to be displayed on the image display unit 4, in concrete terms an orientation mark corresponding to the direction marker of the ultrasonic probe, a body mark which schematically denotes the part of a body including an examination area, or a probe mark which indicates the ultrasonic probe, and the like. As for the orientation images, various marks are prepared and stored, corresponding to various body parts or the types of probes. The operator selects the kind of a body mark or probe mark to be displayed via the input unit 6.

The display system control unit 8 controls display of the orientation image to be displayed on the image display unit 4. In concrete terms, a probe mark is placed at the position corresponding to the position on which the ultrasonic probe is applied (scan surface) on the object, with respect to the selected body mark. The placement of the probe mark is to be set by the operator via the input unit 6. While the display system control unit 8 is shown as a separate component from the control unit 5 in the diagram, the control unit 5 can also have the function of the display system control unit 8.

Figure 3:
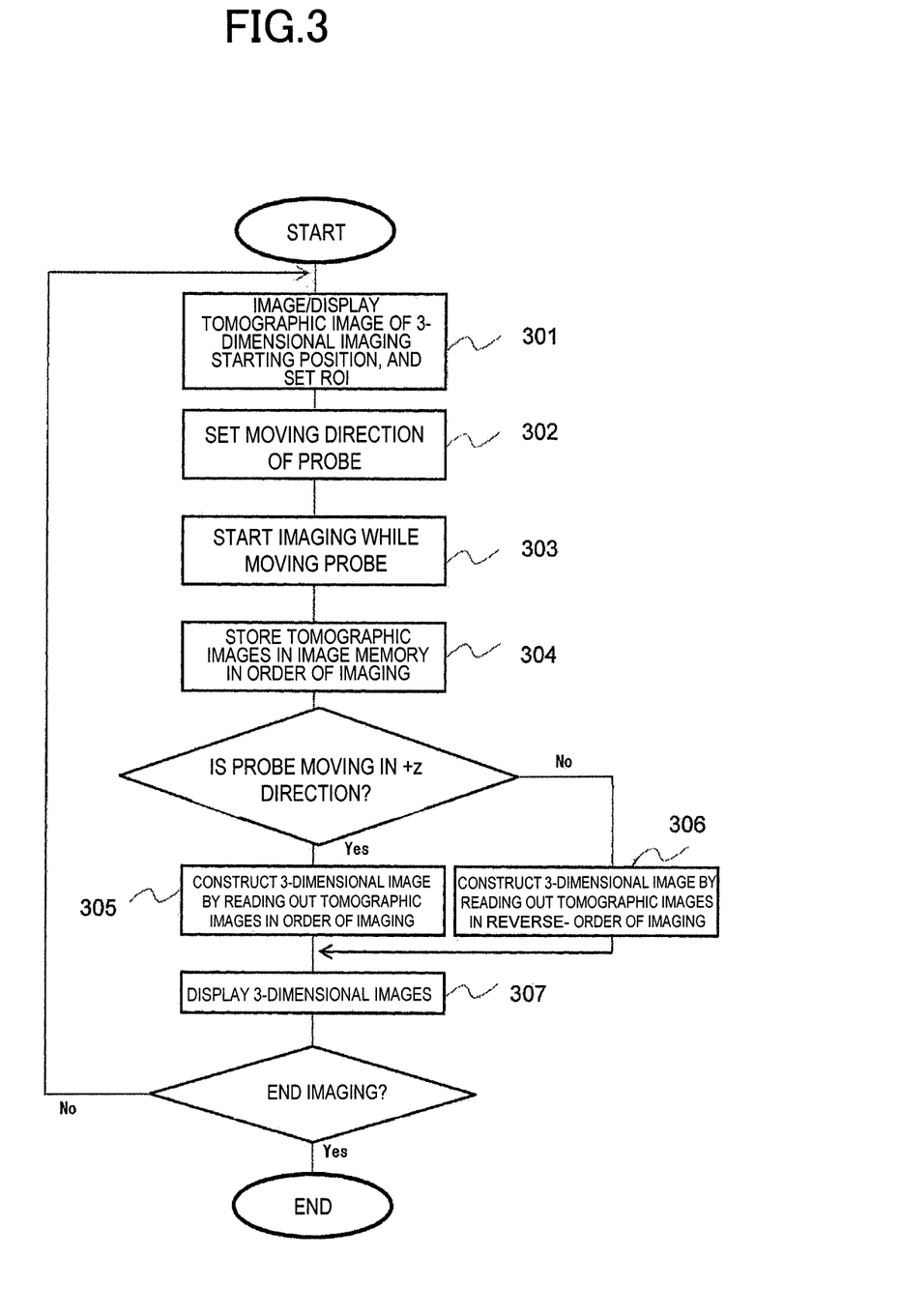
FIG. 3 is a flowchart showing the operation of the ultrasonic imaging apparatus in the first embodiment.

Next, the operation of the above-described ultrasonic imaging apparatus will be described. Imaging operation of tomographic images is the same as that of the conventional ultrasonic imaging apparatuses, thus the procedure of 3-dimensional imaging will be mainly described below. FIG. 3 is a flowchart showing the operation for 3-dimensional imaging.

In 3-dimensional imaging, plural tomographic images are obtained by consecutively imaging while applying the ultrasonic probe 1 to a desired region in an examination target, for example to the surface of a target region and moving the probe in the direction almost orthogonal to the beam scan surface. For this operation, the control unit 5 first obtains a tomographic image in the condition that the ultrasonic probe 1 is applied to the starting position of movement, and displays the image on the image display unit 4 (step 301). The operator confirms whether or not the line-of-sight direction in the tomographic image displayed on the screen of the image display unit 4 is a desired direction, then sets a region of interest (ROI) on the tomographic image and, on the basis of the displayed tomographic image, determines whether to observe the front side of the tomographic image or the back side of the tomographic image, i.e. the moving direction of the ultrasonic probe 1.

Figure 4:
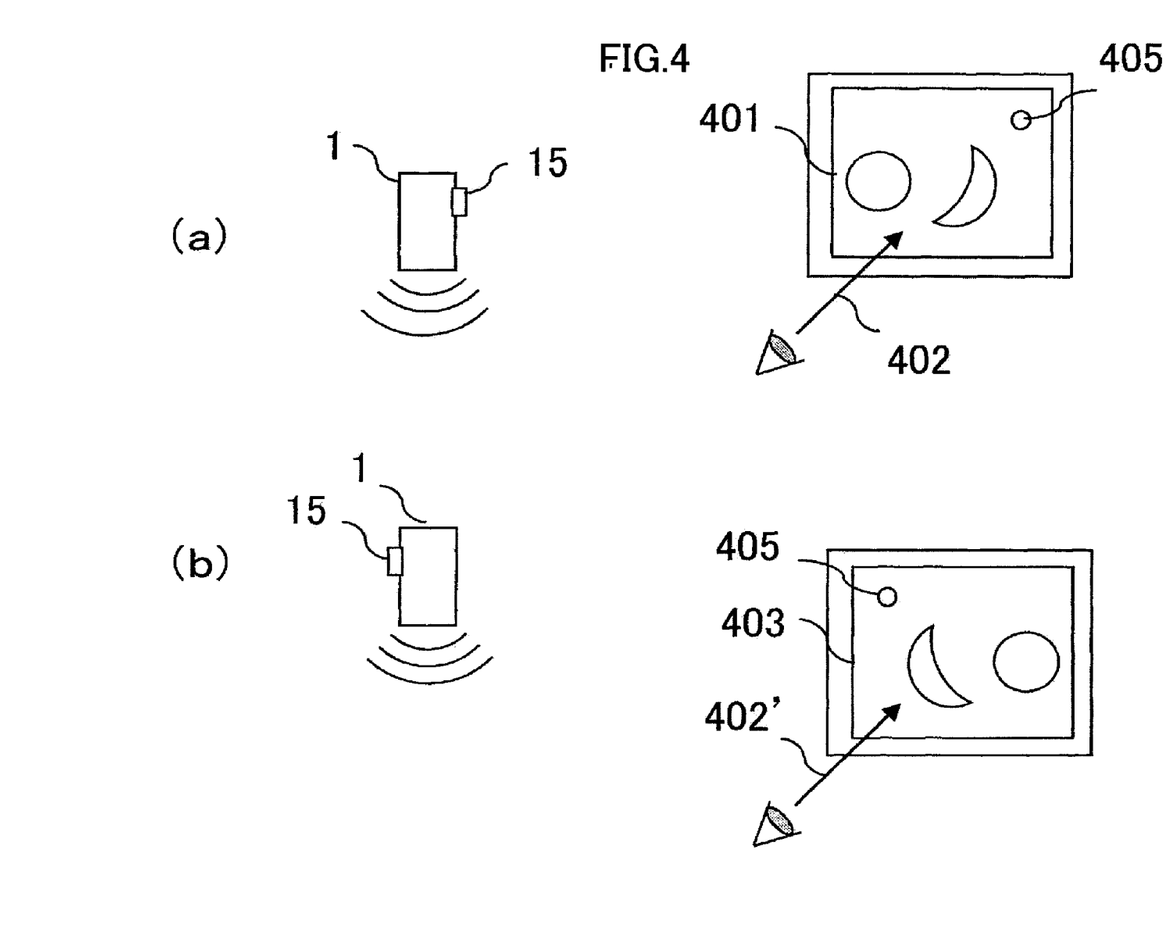
FIG. 4 is the view for explaining the relationship between the orientation of an ultrasonic probe and the line-of-sight direction, in which (a) shows the case that a direction marker of an ultrasonic probe is on the right side as viewed by an operator and (b) shows the case that a direction marker of an ultrasonic probe is on the left side as viewed by an operator.

The line-of-sight direction here means the direction for viewing the scan plane which is a 2-dimensional cross-section either from the adverse side or from the back side, and the operator can arbitrarily switch the direction. For example, as shown in FIG. 4(a), a tomographic image 401 in which the beam scan plane is viewed from the operator's side when it is imaged while the operator held the ultrasonic probe 1 so that a direction marker 15 thereof is on the right side as viewed by the operator, in the case that a line-of-sight direction 402 is switched, can be switched to the tomographic image in which the beam scan plane is viewed from the opposite side. In this case, the line-of-sight direction is the opposite from the subjective line-of-sight direction of the operator. On the other hand, as shown in FIG. 4(b), even when the operator changes the way to hold the ultrasonic probe 1 so that the marker 15 of the probe is on the left side as viewed by the operator and performs imaging, by switching the line-of-sight direction, a tomographic image 403 in which the beam scan surface is viewed from the operator's side can be displayed. Here, a mark 405 corresponding to the direction marker 15 is displayed on the right side of the tomographic image 401 in the case that the tomographic image 401 is displayed (FIG. 4(a)), and the mark 405 corresponding to the direction marker 15 is displayed on the left side of the tomgoraphic image 403 in the case that the tomographic image 403 is displayed (FIG. 4(b)). The operator can confirm the line-of-sight direction by merely confirming whether the mark 405 which is displayed on the screen along with the direction marker 15 of the ultrasonic probe 1 is on the same right side or the left side.

In this manner, after confirming the line-of-sight direction, the operator inputs the moving direction of the ultrasonic probe 1 to the input unit 6.

In concrete terms, the operator sets the moving direction of the ultrasonic probe 1 by setting, while setting the position of the plane (x-y plane) in the tomographic image displayed on the screen as z=0, whether the probe is to be moved from the front toward the back side (in the same direction as the line-of-sight direction) or toward the front side (in the reverse direction to the line-of-sight direction) in the input unit 6 (step 302). Here, the direction which is the same as the line-of-sight direction is defined as +z direction, and the direction opposite from the line-of-sight direction is defined as −z direction.

Next, the control unit 4 executes imaging while the operator moves the ultrasonic probe 1 (step 303). The ultrasonic probe 1 performs beam scanning at a predetermined speed, and the ultrasonic signal conversion unit 3 creates the tomographic image data of the beam scan plane using the echo signals acquired in one time of beam scanning. Though various methods are available for setting an imaging range, generally the moving range of a probe is set by setting the moving distance, collecting time, collecting pitch, etc. via the input unit 6. Tomographic images are collected for the number of collecting time×frame rate (the acquisition number of tomographic images per second). The data of the plural tomographic images collected while moving the ultrasonic probe is sequentially stored in the memory 10 (step 304).

When the operator stops moving the ultrasonic probe 1 and the control unit completes the imaging, the 3-dimensional image construction unit 9 loads the stored plural tomographic images from the image memory 10 and constructs a 3-dimensional image (steps 305 and 306). Here, in step 302, when the moving direction of the ultrasonic probe 1 is set in [+z direction], the order of the tomographic images to be read out from the image memory 10 is made the same as the storage order of the tomographic images stored in the image memory 10 (step 305). On the other hand, when the moving direction of the ultrasonic probe 1 is set in [−z direction], the order of the tomographic images to be read out from the image memory 10 is set opposite to the storage order of the tomographic images stored in the image memory 10 (step 306).

Figure 5:
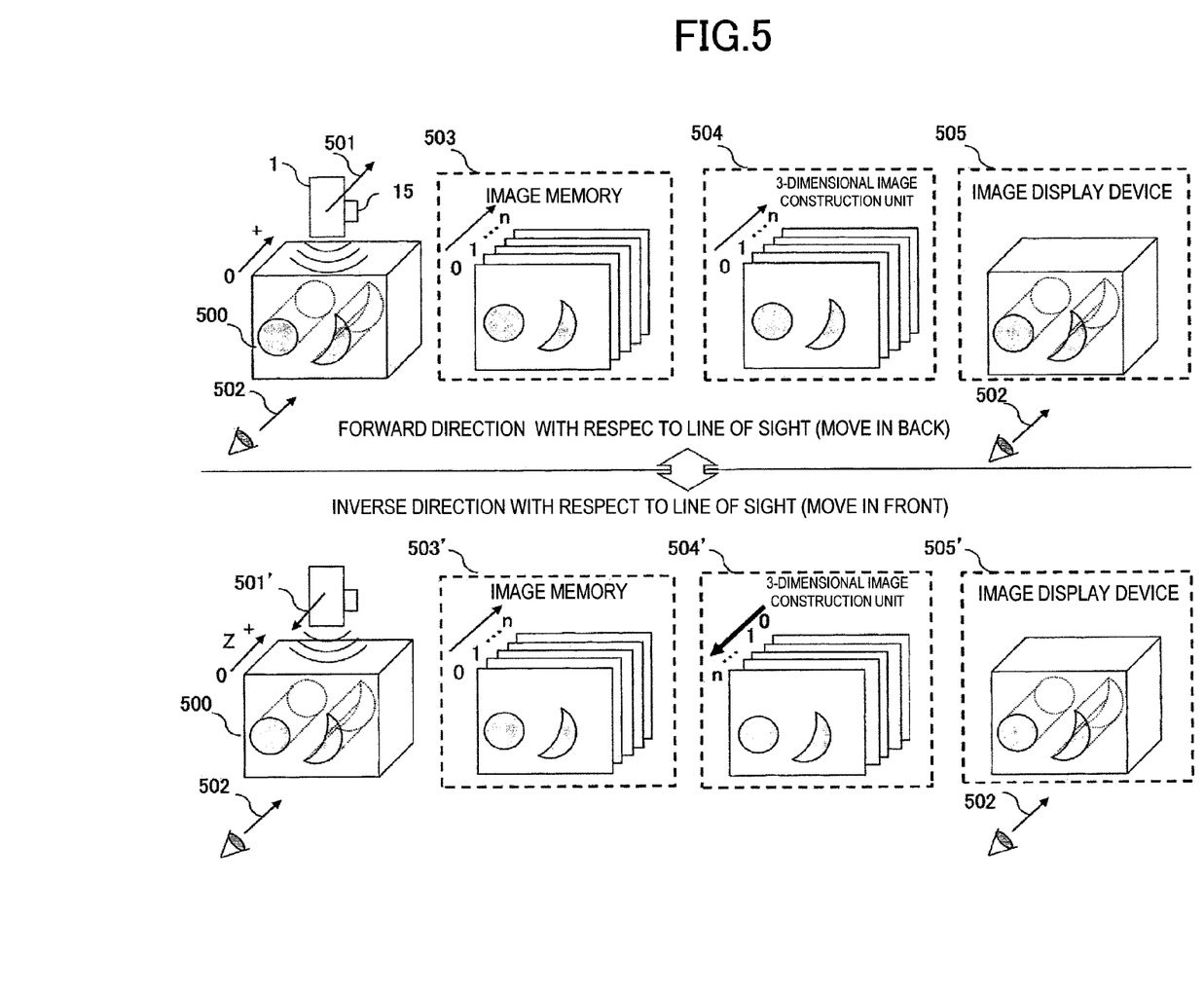
FIG. 5 is a view for explaining image construction in a 3-dimensional image construction unit and the orientation of image display.

FIG. 5 shows the above-described condition. The upper part of FIG. 5 shows the case that a moving direction 501 of the ultrasonic probe is set in [+z direction] which is the same as a line-of-sight direction 502, and the lower part shows the case that a moving direction 501' of the ultrasonic probe is set in [−z direction] which is the opposite direction from a line-of-sight direction 502.

On the far left of each part, the relationship between the moving direction 501 of the ultrasonic probe 1 with respect to an examination target 500 and a line-of-sight direction 502 is illustrated.

As shown in FIG. 5, the fact that the order in which the plural tomographic images are stored in image memories 503 and 503' is the acquisition order of the cross-sections is the same in both cases that the moving direction of the ultrasonic probe is in [+z direction] and in [−z direction]. On the other hand, the order in which the 3-dimensional image constructing unit 9 reads out the cross-sections from the image memory 503 and '503 is the opposite between the cases of [+z direction] and [−z direction]. This means that the cross-sections are consistently arranged from the front of the line-of-sight direction toward the back in 3-dimensional image spaces 504 and '504 that are constructed in the 3-dimensional image constructing unit 9 regardless of the acquisition order of the cross-sections.

Such constructed 3-dimensional images are displayed on the image display unit 4 (step 307). The orientation of display is exactly the way that 3-dimensional images 505 and 505' are constructed in the 3-dimensional image constructing unit 9, thus the image which is positioned at the very front as viewed by the operator is displayed in the very front plane of the 3-dimensional images no matter which direction the ultrasonic probe 1 is moved.

The operator repeats the above-described steps 301–307 as necessary. At that time, what is required of the operator is to simply set the moving direction of the ultrasonic probe 1 based on the image displayed on the screen even when he/she switched the way of holding the ultrasonic probe 1, which enables display of the 3-dimensional images that are consistently viewed from the line-of-sight direction.

As described above, the present embodiment is capable of providing the ultrasonic imaging apparatus which can prevent operators from misidentifying directions, etc. in displayed images by comprising:

an ultrasonic probe;

a transmission/reception circuit configured to transmit and receive ultrasonic signals to/from an object to be examined via the ultrasonic probe;

an image construction unit configured to construct an ultrasonic tomographic image of an examination target using the received ultrasonic signals;

a display unit configured to display the ultrasonic image; and a control unit configured to control the image construction unit and the display unit, further comprising:

a 3-dimensional image construction unit configured to construct a 3-dimensional image using plural ultrasonic tomographic images obtained when the ultrasonic probe is moved in the direction which intersects with the ultrasonic tomographic images; and an ultrasonic probe moving direction setting unit configured to set, on the basis of the ultrasonic tomgoraphic image displayed on the screen of the display unit, a first direction which intersects with the tomographic image or a second direction which is opposite from the first direction, wherein the control unit controls the arrangement order of plural tomographic images in the 3-dimensional image which is constructed in the 3-dimensional image construction unit in accordance with the moving direction of the ultrasonic probe set by the ultrasonic probe moving direction setting unit.

Also, the control unit displays the 3-dimensional image constructed in the 3-dimensional image construction unit on the display image and controls the direction of the displayed 3-dimensional image in accordance with the set moving direction of the ultrasonic probe, thus the ultrasonic imaging apparatus can be provided capable of preventing operators from misidentifying directions in displayed images.

Also, by comprising an input unit as the ultrasonic probe moving direction setting unit for inputting the moving direction of the ultrasonic probe, it is possible to provide the ultrasonic imaging apparatus capable of preventing operators from misidentifying directions in displayed images.

The control unit also constructs a 3-dimensional image by sequentially storing the plural ultrasonic tomographic images obtained along with movement of the ultrasonic probe in the 3-dimensional image space when the moving direction of the ultrasonic probe is the same as the line-of-sight direction with respect to the screen in the display unit, and constructs a 3-dimensional image by storing the plural ultrasonic tomographic images obtained along with movement of the ultrasonic probe in the 3-dimensional image space in the reverse order from the time-series order when the moving direction is the opposite from the line-of-sight direction with respect to the screen of the display unit, thus it is possible to provide the ultrasonic imaging apparatus capable of preventing operators from misidentifying directions in displayed images.

Also, the 3-dimensional image display method using an ultrasonic image in the present embodiment including steps of:

transmitting/receiving ultrasonic signals to/from an object to be examined via an ultrasonic probe;

constructing an ultrasonic tomographic image of the object using the received ultrasonic signals; and displaying the ultrasonic image, further includes steps of:

constructing a 3-dimensional image using the plural ultrasonic tomographic images obtained when the ultrasonic probe is moved in the direction orthogonal to the ultrasonic tomographic images;

setting the ultrasonic probe moving direction, based on the ultrasonic tomographic image displayed on a screen, of either a first direction which intersects with the displayed tomographic image or a second direction which is opposite to the first direction; and controlling the arrangement order of the plural ultrasonic tomographic images in the 3-dimensional image which is constructed in the 3-dimensional construction unit in accordance with the set moving direction of the ultrasonic probe.

In accordance with the present embodiment, the moving direction of an ultrasonic probe is not defined with respect to the physical scan plane of the ultrasonic probe but with respect to the tomgoraphic image displayed on a screen for constructing a 3-dimensional image, thus the chance of setting incorrect directions of the ultrasonic probe can be reduced to a large extent regardless of orientation of the ultrasonic probe, which can lead to prevention of problems in displaying mirrored images or making wrong diagnosis based thereon.

The characteristic effect of the present embodiment is that an operator can perform 3-dimensional imaging while observing only a screen, and the images in which the line-of-sight direction and the display direction are matched can be consistently displayed.

Also in the ultrasonic imaging apparatus comprising a 3-dimensional imaging function, the moving direction of an ultrasonic probe can be set on the basis of a displayed image, i.e. the line-of-sight direction with respect to the image and the image which matches the line-of-sight direction can be displayed, thus it is possible to prevent operators from problems such as specifying wrong moving directions by mistake and display of mirrored images based on the wrong directions can be avoided.

Also in accordance with the present embodiment, by displaying orientation images indicating the moving directions, moving operation of an ultrasonic probe by an operator can be induced and the operator can identify the positional relationship by confirming only the screen of an image display unit without worrying about the way of holding the probe.

Embodiment 2

Figure 6:
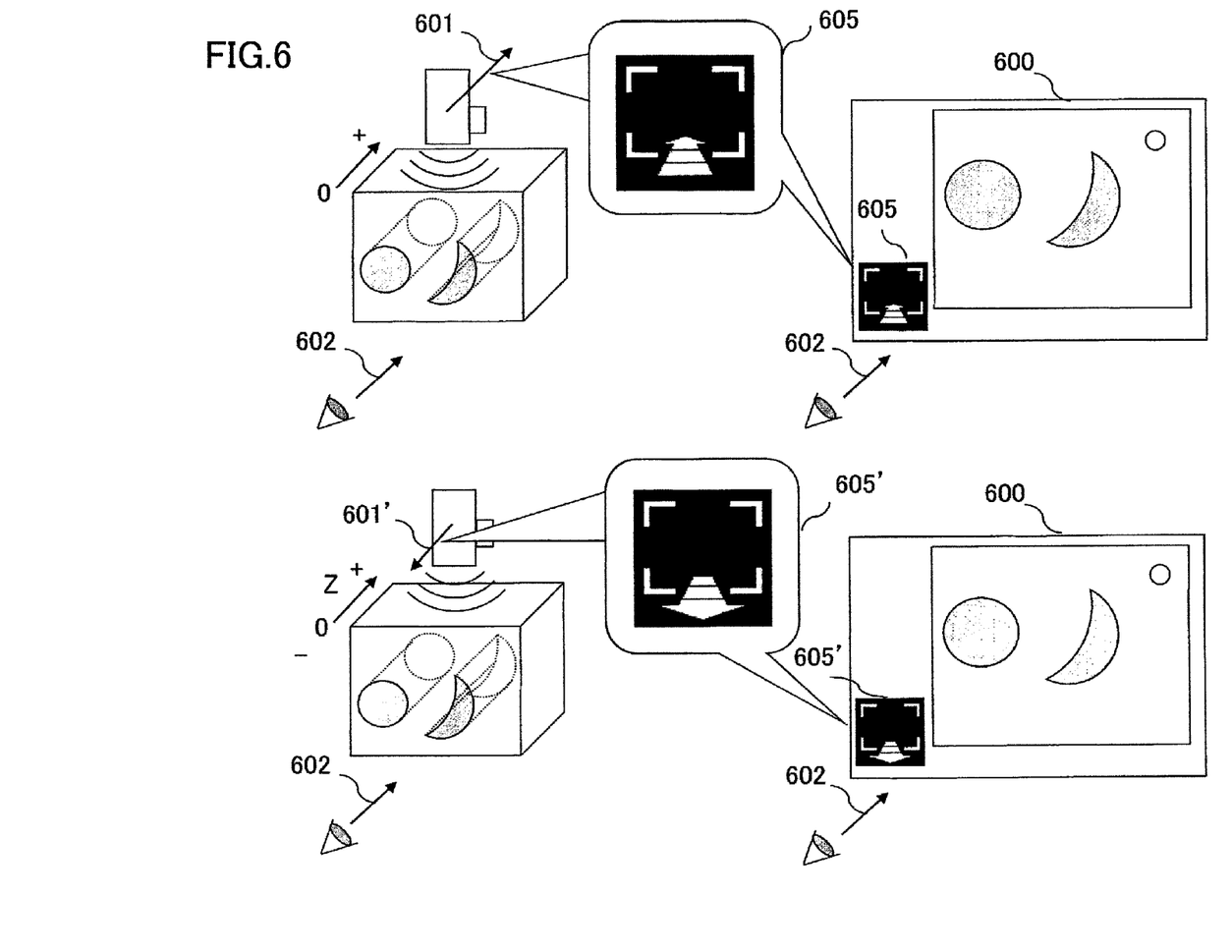
FIG. 6 is a view for explaining a screen display example of the ultrasonic imaging apparatus in a second embodiment.

While the configuration of the ultrasonic imaging apparatus in the present embodiment is the same as the apparatus shown in FIG. 1, the present embodiment is characterized in that a moving direction mark showing the moving direction of the ultrasonic probe 1 which is set via the input unit 6 is displayed in addition to a body mark or a probe mark on the graphic display unit 7 at the time of 3-dimensional imaging. For that purpose, two kinds of moving direction marks corresponding to two moving directions (+z direction and −z direction) are stored in the graphic display unit 7. FIG. 6 shows an example of the direction mark and the state that the direction mark is displayed on a screen along with a tomographic image.

While the procedure of the present embodiment in 3-dimensional imaging is the same as the first embodiment, when the moving direction is set in step 302 of FIG. 3, a direction mark 605 or 605' indicating the moving direction 601 or 601' is displayed on a screen 600 in which a tomographic image 601 is displayed as shown in FIG. 6. In the diagram, in the case that the moving direction is [+z direction] which is the same as a line-of-sight direction 602 (the upper part in the diagram), a direction mark 605 is displayed in which a taper-shaped arrow pointing toward the back side of the tomographic image is depicted. In the case that the moving direction is in [−z direction] which is the opposite from the lineof-sight direction 602 (lower part), a direction mark 605' is displayed in which a club-shaped arrow pointing toward the front side of the tomgraphic image is depicted. The setting of moving direction can be changed via the input unit 6, and the direction mark to be displayed following the moving direction can also be updated.

The rest of the configuration is the same as the first embodiment, thus the explanation thereof is omitted.

The present embodiment comprises an image storage unit configured to store orientation images to be displayed on the display unit, wherein the image storage unit is provided with a moving direction mark image which indicates the moving direction of the ultrasonic probe as the orientation image, and the control unit displays the moving direction mark image along with the ultrasonic tomographic image displayed on the screen of the display unit, whereby movement of the probe with respect to the image displayed on a screen can be indicated to an operator by a direction mark showing the positional relationship in the depth direction so that the operator can recognize the line-of-sight direction more easily and intuitively.

Also, it is preferable in ultrasonic imaging apparatus for making diagnosis, particularly for making real-time diagnosis, to execute a series of operations from extraction of a region of interest on a 2-dimensional image (tomographic image) to construction of 3-dimensional images and diagnosis of 3-dimensional images in the condition that an operator's eyes are fixed on a screen for making effective diagnosis, and the present embodiment is capable of achieving such demand by displaying orientation images which indicate the moving direction of an ultrasonic probe.

Embodiment 3

Figure 7:
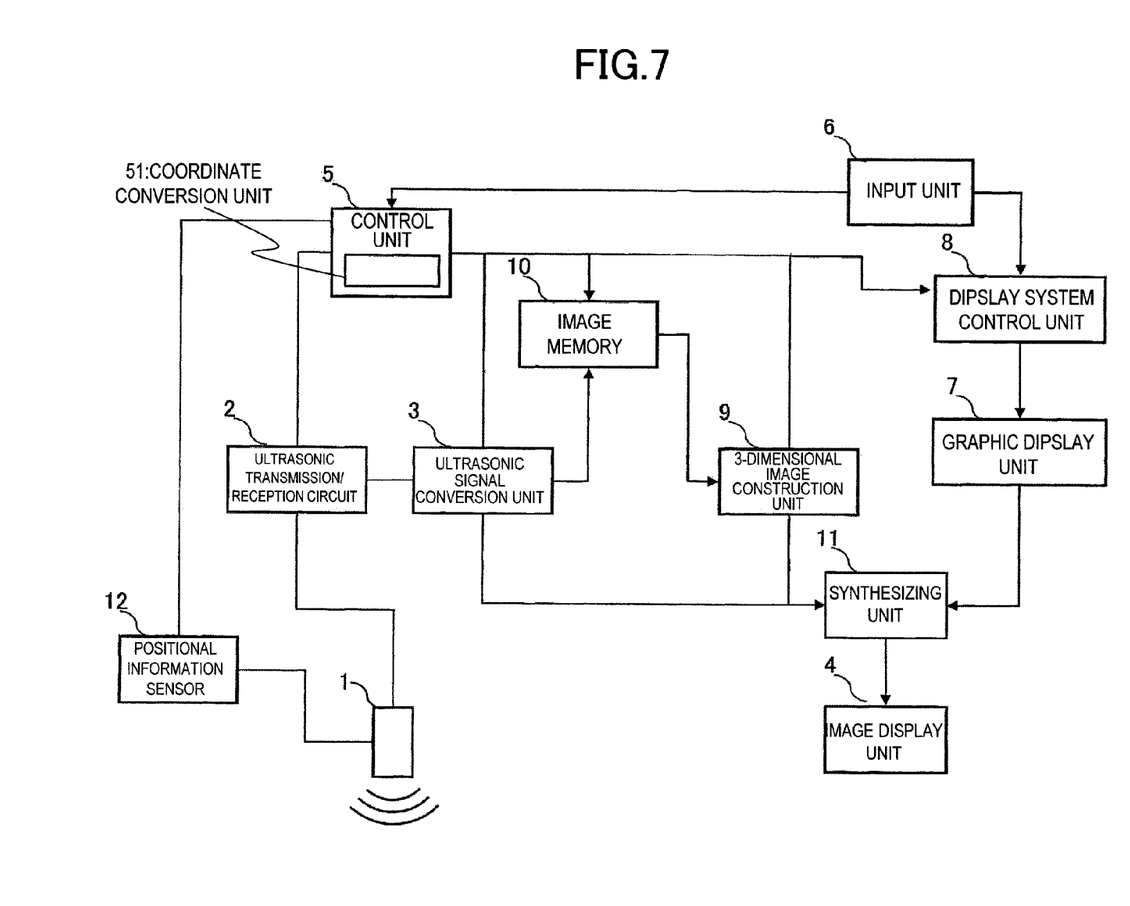
FIG. 7 is a block diagram showing the general outline of the ultrasonic imaging apparatus in a third embodiment.

FIG. 7 shows a general outline of the ultrasonic imaging apparatus in the present embodiment. In FIG. 7, the components denoted by the same reference numerals as the ultrasonic imaging apparatus shown in FIG. 1 have the same function as the ultrasonic imaging apparatus in FIG. 1.

As shown in FIG. 7, the ultrasonic imaging apparatus in the present embodiment is different in comprising a positional information sensor 12 configured to detect the position of the ultrasonic probe 1 in a real space and that the control unit 5 has the function to display the position and the moving direction of the ultrasonic probe 1 in the plane which is approximately parallel to the surface of an examination object, i.e. the plane which is orthogonal to the bean scan plane of the ultrasonic probe 1 on the display unit 12 using the positional information from the positional information sensor 12. In the graphic display unit 7, a moving direction mark for indicating the moving direction is stored besides a body mark or a probe mark.

The present embodiment will be described below focusing mainly on the components that are different from the ultrasonic imaging apparatus shown in FIG. 1.

A commonly-known magnetic, optical or mechanical 3-dimensional position detector can be used for the positional information sensor 12.

The control unit 5 comprises a coordinate conversion unit 51 configured to convert the positional information in a real space which is transmitted from the positional information sensor 12 into the positional information in an image space of an orientation image stored in the graphic display unit 7. The positional information in the coordinate conversion unit 51 is given to the display system control unit 8. The display system control unit 8 adjusts the position of a probe mark and the position or angle of the moving direction mark using the positional information from the coordinate conversion unit 51.

Figure 8:
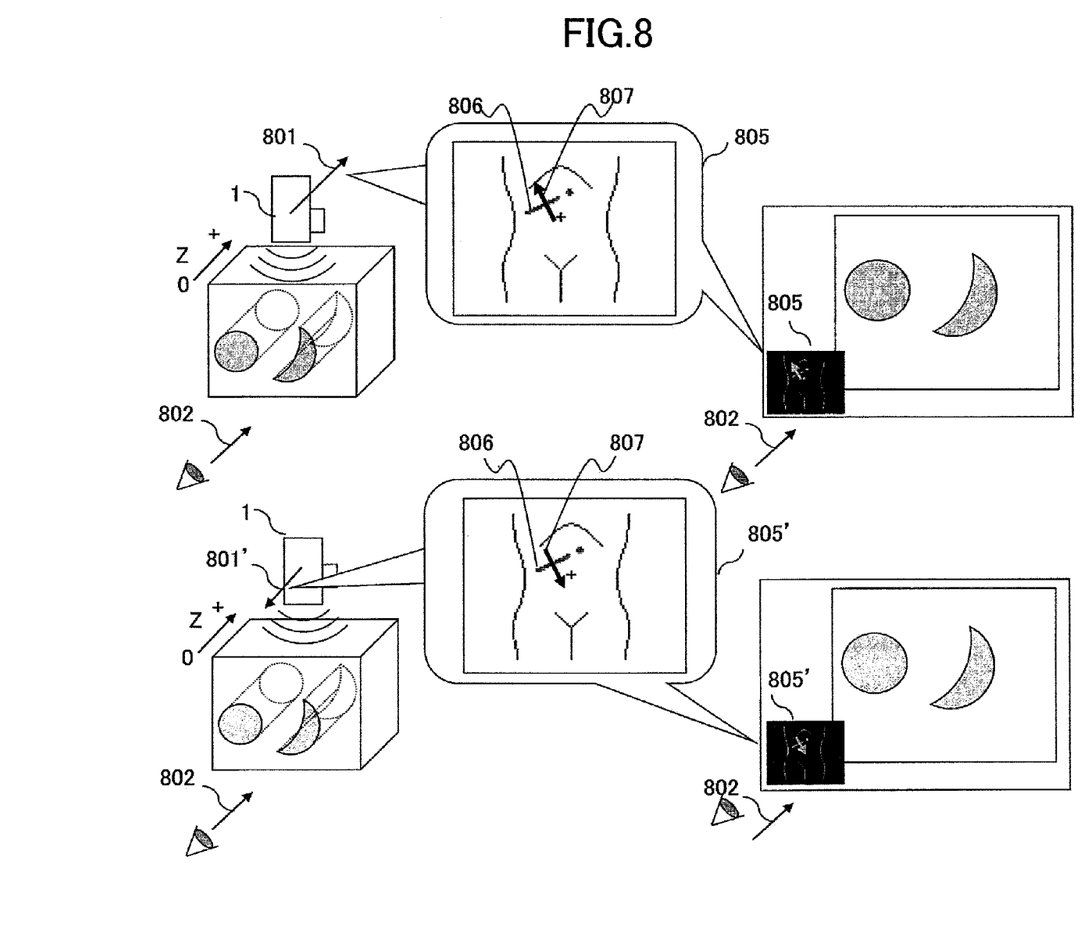
FIG. 8 is a view for explaining a screen display example of the ultrasonic imaging apparatus in the third embodiment.

The operation for 3-dimensional imaging using the ultrasonic imaging apparatus in the present embodiment will be described. As in the first embodiment, a tomographic image of the cross-section at the starting position for 3-dimensional imaging is imaged and displayed in the beginning of the operation. At this time, an orientation image 805 including a body mark is displayed on the screen of the image display unit 4 as shown in FIG. 8. The body mark that suits an examination region is selected to be displayed by an operator from among the orientation images stored in the graphic display unit 7 and displayed. In the example of the diagram, a body mark which indicates an abdominal region of a human body is displayed.

In the meantime, the positional information sensor 12 detects the position of the ultrasonic probe 1 which is placed on the examination region in a real space, and transmits the detected position to the control unit. As for the positional information, 3-dimensional coordinates of the ultrasonic probe after the movement can be calculated, for example by multiplying matrix parameters including the rotation and parallel-movement information while setting a predetermined position in the real space as its origin. The coordinate conversion unit 51 performs coordinate conversion between the coordinates of the ultrasonic probe and the real-space coordinates, as well as between the real-space coordinates and the coordinates of a body mark in an image space, so as to calculate the information on the position and orientation of the ultrasonic probe 1 and send the calculated information to the display system control unit 8. The display system control unit 8 makes a mark (probe mark) 806 which indicates the position of the ultrasonic probe to be depicted on the body mark according to the positional information from the coordinate conversion unit 51. The positional relationship between an object and a body mark can be associated by laying the object (patient) in a predetermined position on a bed. The object can also be associated with the relevant position of a body mark by measuring the position of a region with physical characteristic by the positional information sensor 12.

Next, when the moving direction of the ultrasonic probe 1 is set by the input unit 6, a moving-direction mark 807 which indicates the moving direction 801 of the probe on a body mark. The upper part of FIG. 8 shows the case that the ultrasonic probe 1 is moved in the same direction as a line-of-sight direction 802, and the lower part shows the case that the ultrasonic probe 1 is moved in the reverse direction from the line-of-sight direction 802. A moving direction mark 807 which indicates the difference between the above-mentioned directions by an arrow is displayed on the screen. In this manner, the operator can execute 3-dimensional imaging while observing the screen to confirm the direction for moving the ultrasonic probe 1. Since the movement mark which is displayed on a body mark refers to the moving direction from above, it can be recognized more easily compared to a display mark which indicates the depth direction.

The procedure after the start of 3-dimensional imaging is the same as steps 303~307 that are described in FIG. 3 in the first embodiment. That is, tomographic images are stored in the image memory 10 in order of imaging, a 3-dimensional image is constructed by differing the order of reading out the images from the image memory 10 depending on whether the moving direction of the ultrasonic probe is +z direction or −z direction, and the 3-dimensional image is displayed so that the image in front of the line-of-sight direction is placed in the front side.

The present embodiment comprises a position sensor configured to detect the positional information of an ultrasonic probe in a real space, wherein the control unit displays the position, orientation and the set moving direction of the ultrasonic probe on the orientation image showing an examination target on the basis of the positional information from the position sensor, which enables display of moving direction of the ultrasonic probe with respect to the object and provision of improved operability in addition to the effect in the first and second embodiments.

The present embodiment can improve the operability of the ultrasonic diagnostic apparatus in addition to the effect in the first and second embodiments also by comprising the control unit that displays on the orientation image a movement mark which indicates the range and/or direction in which ultrasonic probe moved on the basis of the positional information from the position sensor.

The ultrasonic diagnostic apparatus of the present embodiment can also display the track or range of the ultrasonic probe 1's actual movement using the positional information of the ultrasonic probe 1.

Figure 9:
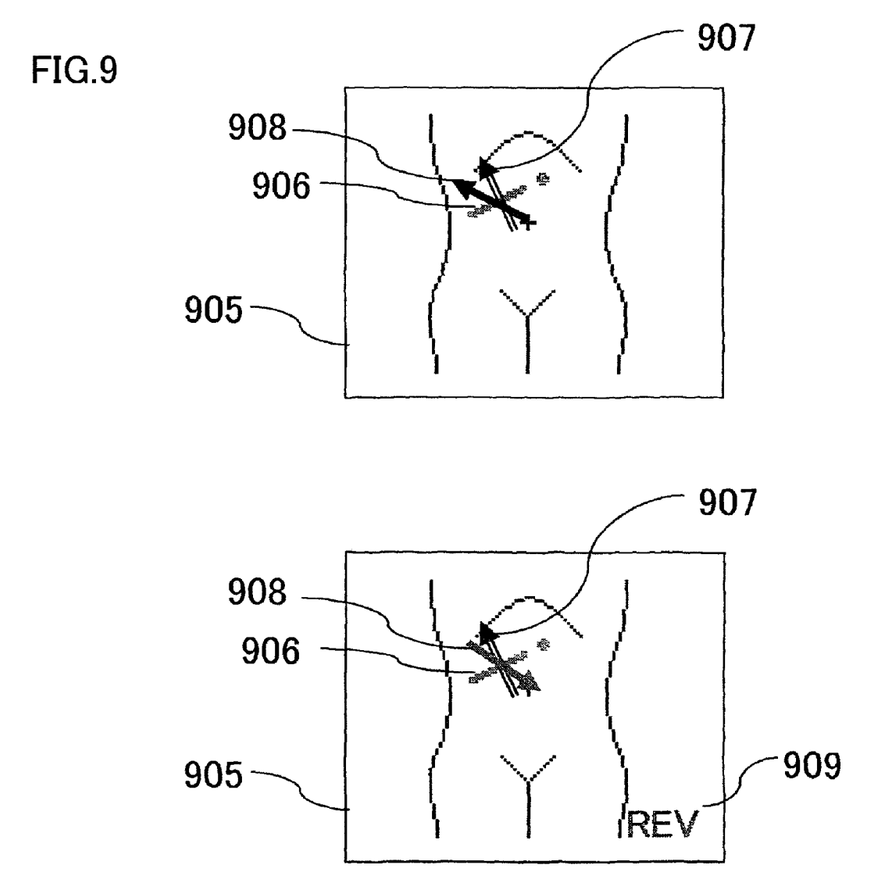
FIG. 9 shows another example of image display in the ultrasonic imaging apparatus in the third embodiment.

FIG. 9 shows an example of a display. In the example shown in the diagram, a movement mark 908 which indicates the direction of the ultrasonic probe's actual movement is displayed on a body mark 905, separately from a moving direction mark 907 to be displayed along with a probe mark 906 at the time that the moving direction of the ultrasonic probe is initially set. In this manner, the operator can confirm whether the ultrasonic probe is moved in the different direction from which he/she intended, and determine whether to perform imaging again. It is possible, when a large displacement from the initial setting is recognized, to draw the attention of the operator by changing the color or blinking the display of the movement mark for enhancement. In the case that the set moving direction is opposite from the actual moving direction, since the display will be reversed, a warning such as the above-described one and/or a string 909, etc. may also be displayed. As for the display, various other methods may be adopted. The moving range of an ultrasonic probe can be represented by the length of an arrow, or a mark which indicates the range can be displayed at the time that the movement is completed.

Also in general, orientation images of a body mark or probe mark, etc. can be not only an index upon imaging but also an effective reference for cross-sectional positions, etc. which are difficult to identify only by tomographic images, by being recorded along with the displayed tomographic image. As described above, by displaying the information of the actual movement of ultrasonic probe 1 as orientation images, it is possible to easily recognize 3-dimensional imaging condition such as the range or direction, etc. of moved areas.

INDUSTRIAL APPLICABILITY

In accordance with the present invention, operability for an operator can be improved in 3-dimensional imaging by an ultrasonic imaging apparatus, and a sequence of operation from diagnosis to image display can be performed while observing a screen. Also, display which can lead to misidentification and wrong diagnosis such as reverse direction display can be prevented.

DESCRIPTION OF REFERENCE NUMERALS 1 ultrasonic probe
2 ultrasonic transmission/reception circuit
3 ultrasonic signal conversion unit
4 image display unit
5 control unit
6 input unit
7 graphic display unit
8 display system control unit
9 3-dimensional image construction unit
10 image memory
11 synthesizing unit
12 positional information sensor
15 direction marker

The invention claimed is:

1. An ultrasonic imaging apparatus, comprising:
an ultrasonic probe including a plurality of transducers arrayed in one direction;
an ultrasonic transmission/reception circuit configured to transmit/receive ultrasonic signals to/from an object to be examined via the ultrasonic probe;
an image constructor configured to construct an ultrasonic two-dimensional tomographic image of the object using the received ultrasonic signals;
a display configured to display the ultrasonic two-dimensional tomographic image;
an inputter configured to receive an input from an operator;
an image memory configured to store the ultrasonic two-dimensional tomographic image constructed by the image constructor;
a controller configured to control the image constructor and the display, the controller including:
a 3-dimensional image constructor configured to construct a 3-dimensional image using a plurality of ultrasonic two-dimensional tomographic images obtained when the ultrasonic probe is moved in a direction orthogonal to the ultrasonic tomographic two-dimensional image;
wherein the inputter includes:
a switch configured to switch a line-of-sight direction of the ultrasonic two-dimensional tomographic image displayed on the display,
an ultrasonic probe moving direction setter configured to set the ultrasonic probe moving direction of either a first direction from a front toward a back side of the display for the operator, or a second direction toward the front side of the display for the operator, after the operator confirms that the ultrasonic two-dimensional tomographic image, displayed on the display, is in a desired direction for the operator;
wherein an order in which the plurality of ultrasonic two-dimensional tomographic images stored in an image memory is a construction order of the ultrasonic two-dimensional tomographic image constructed by the image constructor, and
wherein the 3-dimensional image constructer is further configured to change a reading order of the plurality of ultrasonic tomographic images from the image memory in accordance with the moving direction of the ultrasonic probe which is set by the ultrasonic probe moving direction setter in order that the 3-dimensional image displayed by the display, is displayed in a direction consistent with the direction of the ultrasonic two-dimensional tomographic image displayed by the display.

2. The ultrasonic imaging apparatus of claim 1, wherein the controller is further configured to causes the 3-dimensional image constructed in the 3-dimensional image constructor displayed on the display, and controls the direction of the 3-dimensional image to be displayed in accordance with a set moving direction of the ultrasonic probe.

3. The ultrasonic imaging apparatus of claim 1, wherein the inputter is further configured to input the moving direction of the ultrasonic probe as the ultrasonic probe moving direction setter.

4. The ultrasonic imaging apparatus of claim 1, wherein the controller is further configured to:
constructs the 3-dimensional image by storing in a 3-dimensional image space the plurality of tomographic images that are obtained along with the movement of the ultrasonic probe in a time-series sequence when the moving direction of the ultrasonic probe is the same as the line-of-sight direction with respect to the screen of the display, and
constructs the 3-dimensional image by storing in the 3-dimensional image space the plurality of tomographic images that are obtained along with the movement of the ultrasonic probe in an opposite order from the time-series sequence when the moving direction of the ultrasonic probe is opposite from the line-of-sight direction with respect to the screen of the display.

5. The ultrasonic imaging apparatus of claim 1, wherein the light-of-sight direction is a direction for viewing a scan plane which is the ultrasonic 2-dimensional tomographic images either from an adverse side or from a back side.

6. The ultrasonic imaging apparatus of claim 1, wherein the ultrasonic two-dimensional tomographic image displayed on the display, is in a desired direction for the operator, the desired direction comprising the beam scan surface viewed from the operator's side, is displayed on the display.

7. The ultrasonic imaging apparatus of claim 1, wherein the three dimensional image is displayed in a direction consistent with the direction of the ultrasonic two-dimensional tomographic image displayed by the display, and the ultrasonic two dimensional tomographic images are consistently arranged from the front of the line-of-sight direction toward the back in 3-dimensional image spaces that are constructed in the 3-dimensional image constructor.

8. The ultrasonic imaging apparatus of claim 1, further comprising:
an image storage configured to store orientation images to be displayed on the display;
wherein the image storage includes a moving direction mark image that indicates the moving direction of the ultrasonic probe as an orientation image; and
wherein the controller is further configured to cause the moving direction mark image displayed along with the ultrasonic tomographic image which is displayed on the screen of the display.

9. The ultrasonic imaging apparatus of claim 8, further comprising a positional sensor configured to detect positional information of the ultrasonic probe in a real space, wherein the controller is further configured to cause the position and orientation of the ultrasonic probe and the set ultrasonic probe moving direction displayed on the orientation image showing an examination target, based on the positional information from the positional sensor.

10. The ultrasonic imaging apparatus of claim 9, wherein the controller is further configured to cause a movement mark indicating a range and/or the direction that the ultrasonic probe moved displayed on the orientation image, based on the positional information from the position sensor.

11. A 3-dimensional image display method, using an ultrasonic image, comprising:
transmitting/receiving ultrasonic signals to/from an object to be examined via an ultrasonic probe;
constructing an ultrasonic tomographic image of the object using the received ultrasonic signals;
displaying the ultrasonic image;
constructing a 3-dimensional image using a plurality of ultrasonic tomographic images obtained when the ultrasonic probe is moved in a direction orthogonal to the ultrasonic tomographic image;
setting the ultrasonic probe moving direction of either a first direction, on a basis of the tomographic image displayed on a screen, which is orthogonal to the tomographic image, or a second direction which is opposite from the first direction; and
controlling an arrangement order of the plurality of ultrasonic tomographic images in the constructed 3-dimensional image, in accordance with the set ultrasonic probe moving direction.

12. The 3-dimensional image display method of claim 11, further comprising displaying the constructed 3-dimensional image and controlling the direction of the displayed 3-dimensional image in accordance with the set ultrasonic probe moving direction.

13. The 3-dimensional image display method of claim 11, further comprising inputting the moving direction of the ultrasonic probe.

14. The 3-dimensional image display method of claim 11, further comprising:
constructing a 3-dimensional image by storing in a 3-dimensional image space the plurality of ultrasonic tomographic images obtained along with the movement of the ultrasonic probe in a time-series sequence when the moving direction of the ultrasonic probe is same as a line-of-sight direction with respect to the screen of a display; and
constructing a 3-dimensional image by storing in the 3-dimensional image space the plurality of ultrasonic tomographic images obtained along with the movement of the ultrasonic probe in a reverse order of the time-series sequence when the moving direction is opposite to the line-of-sight direction with respect to the screen.

15. The 3-dimensional image display method of claim 11, further comprising:
storing a moving direction mark image which indicates the moving direction of the ultrasonic probe as an orientation image; and
displaying the orientation image along with the ultrasonic image.

16. The 3-dimensional image display method of claim 15, further comprising:
detecting positional information of the ultrasonic probe in a real space; and
displaying position and orientation of the ultrasonic probe and the set moving direction of the ultrasonic probe on the orientation image showing an examination object, on the basis of the positional information.

17. The 3-dimensional image display method of claim 16, further comprising displaying on the orientation image a movement mark indicating a range and/or the direction that the ultrasonic probe moved, on the basis of the positional information.

* * * * *